United States Patent
Dixon et al.

(10) Patent No.: US 6,645,207 B2
(45) Date of Patent: Nov. 11, 2003

(54) METHOD AND APPARATUS FOR DYNAMIZED SPINAL STABILIZATION

(76) Inventors: Robert A. Dixon, 10577 Durham Pl, Powell, OH (US) 43065; Donald J. Hackman, 3499 Kirkham Rd., Columbus, OH (US) 43221

( * ) Notice: Subject to any disclaimer, the term of this patent is extended or adjusted under 35 U.S.C. 154(b) by 26 days.

(21) Appl. No.: 09/846,956

(22) Filed: May 1, 2001

(65) Prior Publication Data

US 2001/0037111 A1 Nov. 1, 2001

Related U.S. Application Data

(60) Provisional application No. 60/202,422, filed on May 8, 2000.

(51) Int. Cl.$^7$ ............................................. A61B 17/70
(52) U.S. Cl. ........................................ 606/61; 606/72
(58) Field of Search ............................. 606/60, 61, 69, 606/72, 70, 73, 71, 105

(56) References Cited

U.S. PATENT DOCUMENTS

| | | | | |
|---|---|---|---|---|
| 4,790,297 A | * | 12/1988 | Luque | 606/61 |
| 4,913,134 A | * | 4/1990 | Luque | 606/61 |
| 5,084,049 A | | 1/1992 | Asher et al. | |
| 5,290,288 A | * | 3/1994 | Vignaud et al. | 606/61 |
| 5,330,473 A | * | 7/1994 | Howland | 403/396 |
| 5,380,325 A | | 1/1995 | Lahille et al. | |
| 5,498,263 A | * | 3/1996 | DiNello et al. | 403/3 |
| 5,545,163 A | | 8/1996 | Miller et al. | |
| 5,584,887 A | * | 12/1996 | Kambin | 606/61 |
| 5,613,967 A | | 3/1997 | Engelhardt et al. | |
| 5,702,395 A | * | 12/1997 | Hopf | 606/61 |
| 5,728,127 A | * | 3/1998 | Asher et al. | 606/61 |
| 5,947,965 A | | 9/1999 | Bryan | |
| 6,136,002 A | * | 10/2000 | Shih et al. | 606/61 |
| 6,315,779 B1 | * | 11/2001 | Morrison et al. | 606/60 |

OTHER PUBLICATIONS

Patrick W. Hitchon, MD, et al., "Biomechanical Studies of a Dynamized Anterior Thoracolumbar implant" Spine, 2000, pp 306–309, vol. 25, No. 3, Lippincott Williams & Wilkins, Inc. Philadelphia, PA.
Twinflex (R), Claris Surgical Technique, Spine Network Group of Companies (Brochure).
Spinal Clip System OrthoTech Distributed by REO Spine-Line Morgantown WV. (Brochure).
Spinal Fixation System, Blackstone (TM) Medical Inc. Springfield, Massachusetts (Brochure).
DOC Ventral Cervical Stabilization System, DePuy Acromed Co (Brochure).
Solid Connection System (TM) Spinal System, Aesculap (R) Co South San Francisco, CA (Brochure).

* cited by examiner

*Primary Examiner*—Kevin Shaver
*Assistant Examiner*—Michael B. Priddy

(57) ABSTRACT

An improved device and a method for stabilizing lumbar vertebrae in a human spine for the purpose of fixing the vertebra with respect to other vertebra and with respect to other parts of the spinal column. This device comprises a plate, bone screws, bone screw clamp portion, spacers, and rigidizing stop locks. The bone screw clamps may be clamped firmly to the plate for a fully rigid system. Alternatively the screw clamp portions may be held apart, with clearance between them and the plate, which will allow for axial motion of the screw with respect to the plate for implant load sharing and dynamized motion.

8 Claims, 4 Drawing Sheets

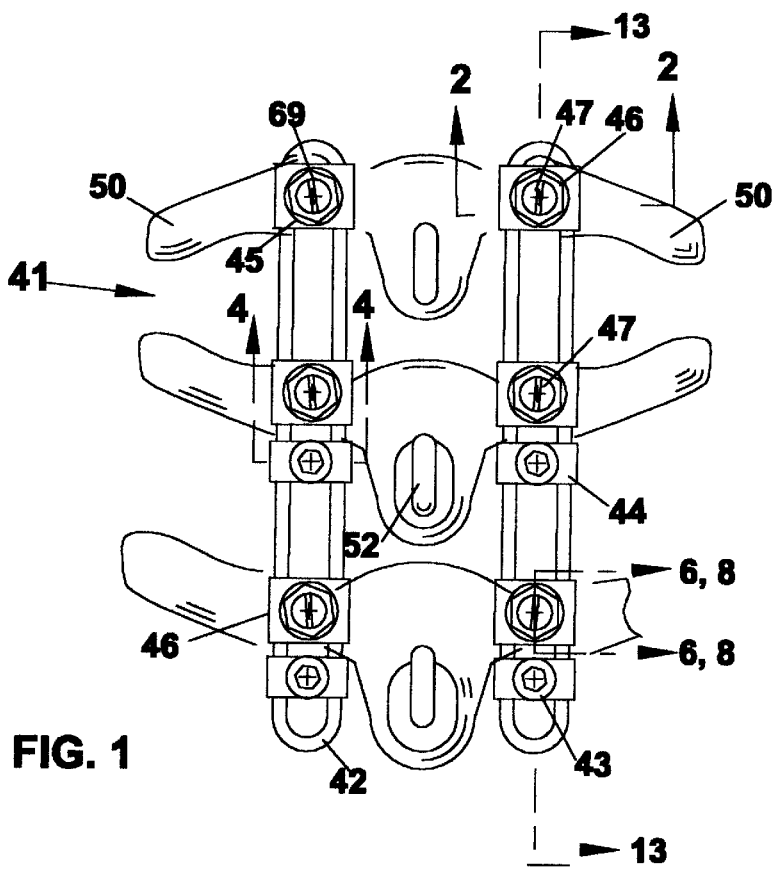
FIG. 1
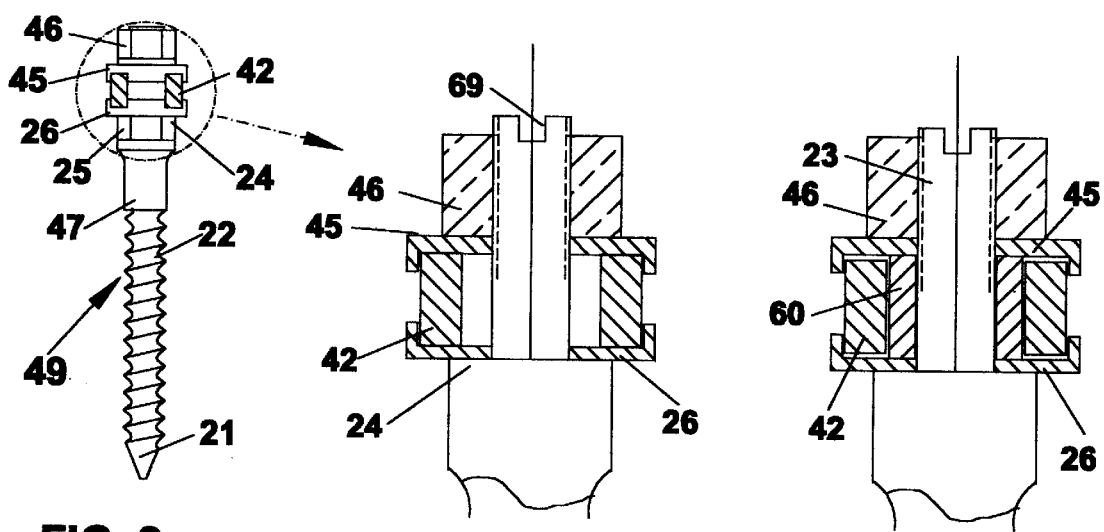
FIG. 2  FIG. 3  FIG. 3a

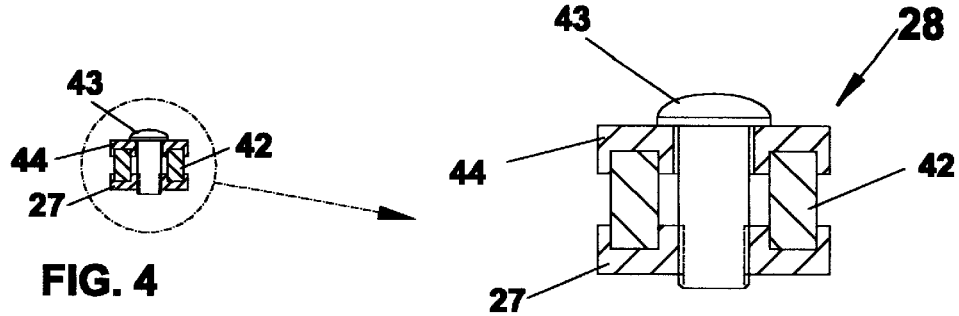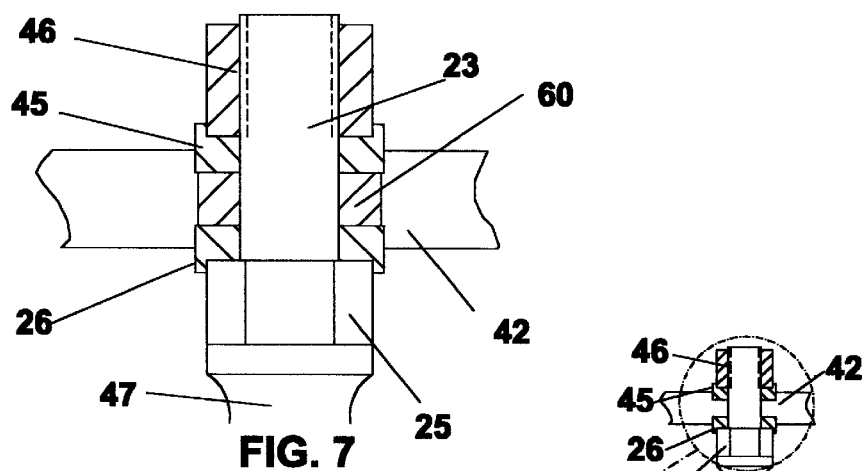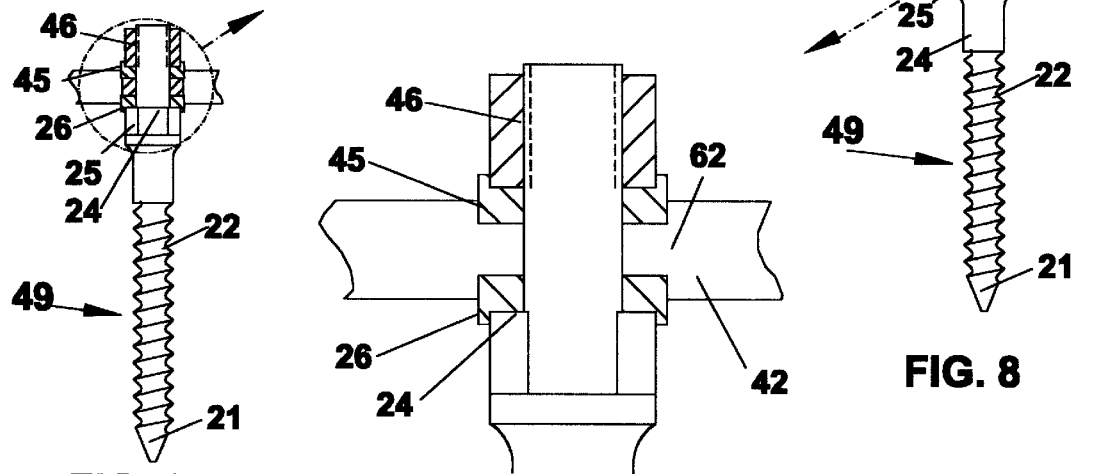

METHOD AND APPARATUS FOR DYNAMIZED SPINAL STABILIZATION

CROSS-REFERENCES TO RELATED APPLICATIONS

This patent application was preceded by: Provisional Patent No. 60/202,422 with a file date of May 8, 2000.

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

Spinal fusions are performed to treat degenerative diseases, deformities, and trauma. These problems generally cause or allow displacement or rotation of a vertebra relative to the adjacent vertebra. The objective of spinal implants is to facilitate realignment and/or fixation of spinal elements for fusion. In clinical studies it has been demonstrated that surgeries using spinal implants are more effective at providing structure and rigidity to the spine than surgeries in which implants are not used. Since their introduction as crude plates, rods, and wires, these devices have been developed into sophisticated appliances, which can be assembled and configured to rigidize spines of any size or condition. These devices provide a mechanical fixation for restraint of an implanted graft material. With this fixation, displacement of the disc graft material is significantly reduced. The majority of existing lumbar implants use round rods with pedicle screws threaded into the vertebra and clamped to the rod. Round rod assemblies use clamps or set screws to fix collars to the round rods. Round attachments tend to rotate around round rods and they depend on friction to resist torsion. These components are less rigid in torsion. Rectangular shaped devices better lend themselves to restrict rotational motion. The devices have been costly due to the complexity, which requires accurately machined components. Many of the existing devices require bone screw anti-rotational stops or locks to prevent the bone screw from unscrewing from the bone. Recent studies as well as time honored principles (Wolff's Law), have shown that a device, that will allow the fusion joint to remain in compression, will tend to lessen distraction and reduce the fusion time. In the literature this motion is referred to as "dynamized" motion. It is believed that compression will reduce the fusion time by reducing the stretching rupture and shear of the forming nutrient blood vessels.

Over time anterior or posterior spinal implants, which are stabilized with fixed rigid constructs have resulted in graft and implant failure and breakage. This is due to stress shielding of the healing bone by the rigid construct. Axial stress shielding results in failure of the bone to heal (failure of fusion), or development of a weak fusion unable to support the full physiologic forces. Semi rigid constructs have been developed to allow partial loading of the healing bone. These semi-rigid implants allow semi-rigidity in all 6 planes of motion thereby allowing harmful shear motion as well. Shear motions destroy the ingrowing nutrient vessels and can result in graft failure. Most semi rigid systems available are poor at allowing axial subsidence thereby poor at load sharing. To reduce the occurrence of axial stress shielding (thereby increasing load sharing by the graft), better implant devices are needed. These devices should collapse or freely move axially to allow normal linear subsidence of the vertebra and the graft, but still restrict motion in shear directions. These devices should allow the total load from the ligament tension and the weight above the graft to act upon the fusion interface resulting in a higher fusion rate and stronger fusion development. These devices are sometimes referred to as "dynamic" or "dynamized". The following patents are typical of other patents in this field:

Steffee (U.S. Pat. No. 4,719,905) describes an apparatus including a rod, clamps, and fastener assemblies for securing the rod to a spinal column.

Puno et al. (U.S. Pat. No. 4,805,602) utilizes an apparatus for the internal fixation of the spine. The apparatus includes two sets of implants each consisting of a rod and vertebral anchors.

Heinig et al. (U.S. Pat. No. 4,887,595) describes a plate and screw system for maintaining the relative position of the spinal bodies of a spinal column.

Sherman (U.S. Pat. No. 4,887,596) describes a pedicle screw for use in internal fixation of the spine.

Asher et al. (U.S. Pat. No. 5,084,049) describes a pair of corrective devices for securement to a spinal column. Each device includes a spine plate having a plurality of openings for receiving a fastener to connect the spine plate to a vertebra Dubousset (U.S. Pat. No. 5,147,360) describes a device for correction of spinal curvature with anterior and posterior rods are fixed to the vertebral bodies to apply the necessary corrective forces to the spinal column.

Cotrel (U.S. Pat. No. 5,154,719) describes an implant for osteosynthesis, the implant being in the form of a screw having a rod-receiving head.

Mehdian (U.S. Pat. No. 5,217,497) describes an implant for fixing one segment of a spinal column to another segment, the implant in the form of a screw having a slotted head to which a support rod is anchored.

Ashman (U.S. Pat. No. 5,242,445) describes an eyebolt having two shell-like portions for engagement to a spinal rod.

Vignaud et al. (U.S. Pat. No. 5,261,907) describes an interconnecting device able to lock two spinal fasteners.

Wagner (U.S. Pat. No. 5,334,203) describes a construct using surgical rods and connectors. The connector includes a plate with a pair of double hook bolts to secure the plate to the surgical rods.

Engelhardt et al. (U.S. Pat. No. 5,613,967) describes an apparatus with a slotted plate with pedicle screws which are clamped together with an interference fit which will not allow free subsidence and stress shields all six motions.

Martin (U.S. Pat. No. 5,672,175 describes an implant places a constant force upon the vertebra to correct orthosis. This device does not give shear stress shielding required for fusion.

Many patents have been issued for spinal fixation devices, however none have the free 12 subsidence dynamized action feature. Most of these devices use a rod or a plate with pedicle screws threaded into the vertebra. They mainly differ in the mechanical means to attach the screws to the to the rods or plates. Many enable the surgeon to selectively adjust the alignment of the patient's spine and then to secure that alignment with the spine fixation device. Further, due to the wide variation in spinal dimensions and availability of suitable attachment sites, most devices have limited application.

It would be a significant improvement to provide a spinal fixation apparatus and methods that would allow normal subsidence with the total force acting in axial compression on the graft, but would give stress shielding in the other five motions. It should allow the surgeon to select the vertebrae that require dymization and easily and quickly implement it. Such a novel spinal fixation apparatus and method is disclosed and claimed in this patent

BRIEF SUMMARY OF THE INVENTION

This invention relates to an improved spinal stabilizing device, and a method of implanting it on the posterior, anterior, or lateral side of the lumbar spine. This device employs rectangular plate sections that allow axial subsiding motion without rotation and will allow continuous axial load sharing with the implant, without the need for accurately machined components. It is easily adapted and manipulated to fix the vertebrae or allow selected axial subsiding motion by the surgeon at the time of implantation. This device comprises a plate, bone screws, bone screw clamp portions, spacers, and rigidizing-stop locks. The bone screw clamp portions may be clamped firmly to the plate for a fully rigid system. Alternatively the screw clamp portions may be held apart, with clearance between them and the plate, by selectively installing clamp spacers. These spacers will allow for bone screw axial motion with respect to the plate, allowing for dynamized motion and load sharing. Compression clamping allows maintenance of compression. This allows only subsidence and prevents potentially damaging distraction of the graft vertebral interface. This contact interface is crucial to graft ingrowth of nutrient vessels. Described is a lumbar system connected by a pedicle screw construct. The pedicle screws and plates are not the focus of this patent and are considered as prior art.

BRIEF DESCRIPTION OF THE SEVERAL VIEWS OF THE DRAWINGS

The present invention will be better understood from the following detailed description of the preferred embodiment. This is not to infer that this is the only embodiment for which this device concept may be used. In the accompanying drawings the reference numbers refer to the individual parts described in the text.

FIG. 1 is a plan view of the dynamized spinal stabilization system shown on the lumbar portion of a human spinal column attached to posterior vertebra, with bone screws through the pedicle structure.

FIG. 2 is a cross-section of the bone screw taken along the line 2—2 of FIG. 1

FIG. 3 is an enlarged section of the bone screw and the bone screw clamp taken from the encircled area of FIG. 2:

FIG 3a is an enlarged section view of the bone screw and the bone screw clamps, with a spacer inserted, taken from the encircled area of FIG. 2

FIG. 4 is a section view of the rigidizing stop lock taken along the line 4—4 of FIG. 1:

FIG. 5 is an enlarged view of FIG. 4

FIG. 6 is a partial section of the bone screw with a spacer, inserted for dynamized action, taken along the line 6—6 of FIG. 1.

FIG. 7 is an enlarged section of FIG. 6

FIG. 8 is a partial section of the bone screw with the spacer removed for a fixed configuration, taken along the line 8—8 of FIG. 1.

FIG. 9 is an enlarged section of FIG. 8

DETAILED DESCRIPTION OF THE INVENTION

Figure 10:
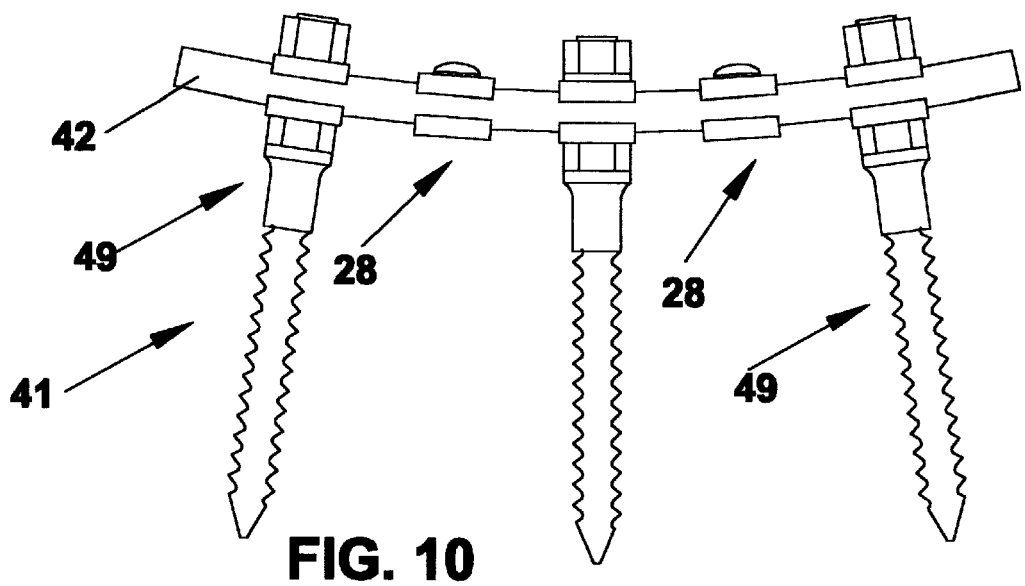
FIG. 10 is a side (lateral) view of the dynamized spinal stabilization system using a curved plate.

In the description of the bone screw clamps and the rigidizing stop lock clamp portions upper and lower refers to the surgeon's view with a patient lying face down on the operating table. It is also understood that "fixed" and "rigid" are relative terms not implying zero measurable motion, but much less motion relative to the adjacent vertebra before installation of the stabilizer system. For simplification the stabilizer system is described as a lumbar stabilizer in one of many conceivable embodiments. That is not to imply that this is the only embodiment within which the stabilizing system can be configured. The components may be fabricated from metal, preferably titanium or a titanium alloy. The components may also be fabricated from other metals. This system is shown with a plate, bone screws, and, nuts from the Eurosurgical pedicle screw lumbar system distributed in the U.S. by REO Spineline. However this dynamized system can be adapted to any slotted plate or dual rod pedicle screw system.

The Dynamized Spinal Stabilization System

The present invention describes an improved device and a method for stabilizing lumbar vertebrae in a human spine for the purpose of fixing the vertebra with respect to other vertebrae or interposing device or substance and with respect to other parts of the spinal column. In the preferred embodiment, shown in FIG. 1 and FIG. 13, the system is attached at the posterior surface of the spine. The total system 41 may be modified for use on the anterior or lateral sides of the lumbar spine. The system comprises a plate 42, bone connector assemblies 49, bone connector clamp portions 45 and 26, bone connector spacers 60, and rigidizing-stop locks 28 as shown in FIG. 1. The system 41 and its components are described in the following paragraphs. The bone stabilizing method of implanting is described in a subsequent section of this document.

The Plate

Figure 11:
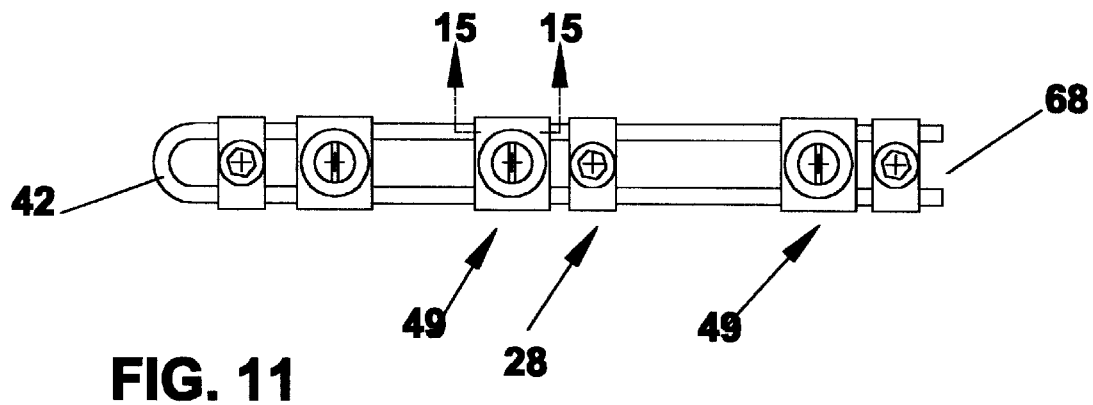
FIG. 11 is a plan view of the dynamized spinal stabilization system with an optional opened-ended plate, which will allow the plate to be cut to length during surgery.

The plate 42 is the framework upon which the other components are attached. The plate has a slot parallel to its longitudinal axis to receive and contain the bone screws. In the preferred embodiment the plate 42 is machined from a single piece of metal. Unlike stabilizing plates with pre-formed holes that dictate the location of the bone screws, this invention allows the bone screws 47 to be infinitely positioned axially to place it into the desired position of the vertebra as shown in FIG. 1. The plate may be curved or shaped to allow for stabilizing the spine or positioning individual vertebra as required. The plate may have an open end 68 as shown in FIG. 11. This open end will allow one piece sliding bone screw clamps to be inserted. The open end may be closed and stiffened with rigidizing stop locks.

The Bone Connector

In the preferred embodiment the bone connector, shown in FIG. 2, will subsequently be referred to as a bone screw. The bone screw has tapered screw threads 22 at the bone end 21, a head which will accept a tool near the midsection 25, and a machine screw threaded stud 48 at the clamp end. Alternatively, in place of the bone screw, other attachment means such as straight pins or tapered pins may be pressed into or bonded to the bone. Bone hooks may also be used for bone attachments. The bone screw also has a screwdriver slot to adjust the screw height as shown in FIG. 3.

Bone Screw Clamp

The bone screw 47 is attached to the plate 42 with the bone screw clamp portion 45 and 26, shown in FIG. 3. The clamp comprises an upper portion 45, a lower portion 26, and a machine screw nut 46. The nut 46 clamps the upper portion 45, through the plate 42 or rod, to the lower portion 26 and against a shoulder 24 on the bone screw 47 to give metal-to-metal clamping. Because of the metal-to-metal clamping the bone screw 47 does not require anti-rotational locks such as auxiliary screw clamps, cams, wedges or locking caps. The metal-to-metal clamping of the bone screw 47 to the plate provides a fully rigid bone stabilizer system.

Figure 12:
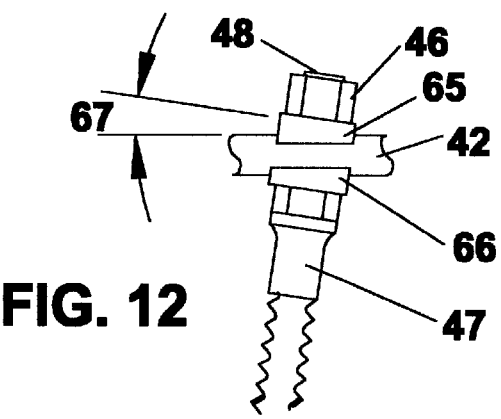
FIG. 12 is a side view of the system using the optional angled bone screw clamp.

The bone screw clamp portions may be machined to angular shapes 65 and 66 to allow the bone screw to be attached to the plate at an angle 67 shown in FIG. 12.

Spacer

Figure 16:
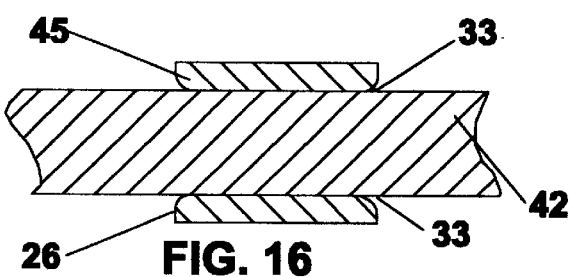
FIG. 16 is an enlarged section of FIG. 15.

In a rigid installation the nut 46 (shown in FIG. 7) forces the bone screw clamp portions 45 and 26 to the plate 42. Selectively installing spacers 60 between the clamp portion 45 and 26 will allow axial motion of the bone screw assembly 49 along the slot with respect to the plate 42. This axial motion provides dynamized action between the bone screw assembly 49 and the plate 42. Because of the metal-to-metal clamping through the spacer 60 there is no need for auxiliary screw clamps such as a cam, a wedge or a locking cap. The bone screw clamps should have radii 33, as shown in FIG. 16, at the ends that contact plate 42 to reduce stress concentrations in the plate. To reduce the number of small parts the sliding bone lower clamp, the lower clamp and the spacer may be fabricated as one integral part. This clamp would require an open ended plate 68 as shown in FIG. 11.

Rigidizing Stop Locks

The rigidizing stop lock assemblies 28, as shown in FIG. 10, are clamped to the plate 42 to maintain plate rigidity and they may serve as travel limit stops 30 for unidirectional dynamized (subsidence) action of the bone screw assembly 49 with respect to the plate 42. The rigidizing stop lock includes an upper portion 44 a lower portion 27 and a screw 43. This unidirectional dynamized action allows subsidence of the vertebra 51. This allows for any graft resorption and settling. It also provides improved fusion conditions and prevents graft distraction. The rigidizing stop locks 28 may be preloaded before tightening the stop lock screw 43. The stop locks may utilize springs or other force generating means to maintain compression on the vertebra/graft interface.

Stress Shielding

Physical science teaches that a single object of matter can be moved in no more than six motions, three axial motions and three rotational motions. The present invention will provide stress shielding to the vertebra in five or all six of the directions of motion. The stabilizing system will provide stress shielding from the following vertebral motions:
(a) Rotation causing axial shear
(b) Lateral bending causing contralateral distraction
(c) Flexion causing posterior distraction
(d) Extension causing anterior distraction
(e) Horizontal force causing translation shear
(f) It will also stress shield the stabilized vertebra from extension causing distraction.

However it will allow for axial subsidence or compression at the fusion interface of the stabilized vertebra, bone, graft, or other device or substance. This compression is desirable because it tends to prevent lateral motion at the fusion interface and promotes improved vascularization of the graft.

Bone Stabilizer Implanting Method

In the preferred embodiment the stabilizer (FIGS. 1 and 13) may be used in pairs lateral to the spinous process 52, attached medial of the transverse process 50 with the bone screws 47 threaded into the pedicle 53 from a posterior opening. Because of the length of the pedicle 53 structure, the bone screws 47 will give greater fixation at this location. The system may also be used singularly to either side of the spinous process 52. The adjacent 55 disc is shown in FIG. 13.

Figure 13:
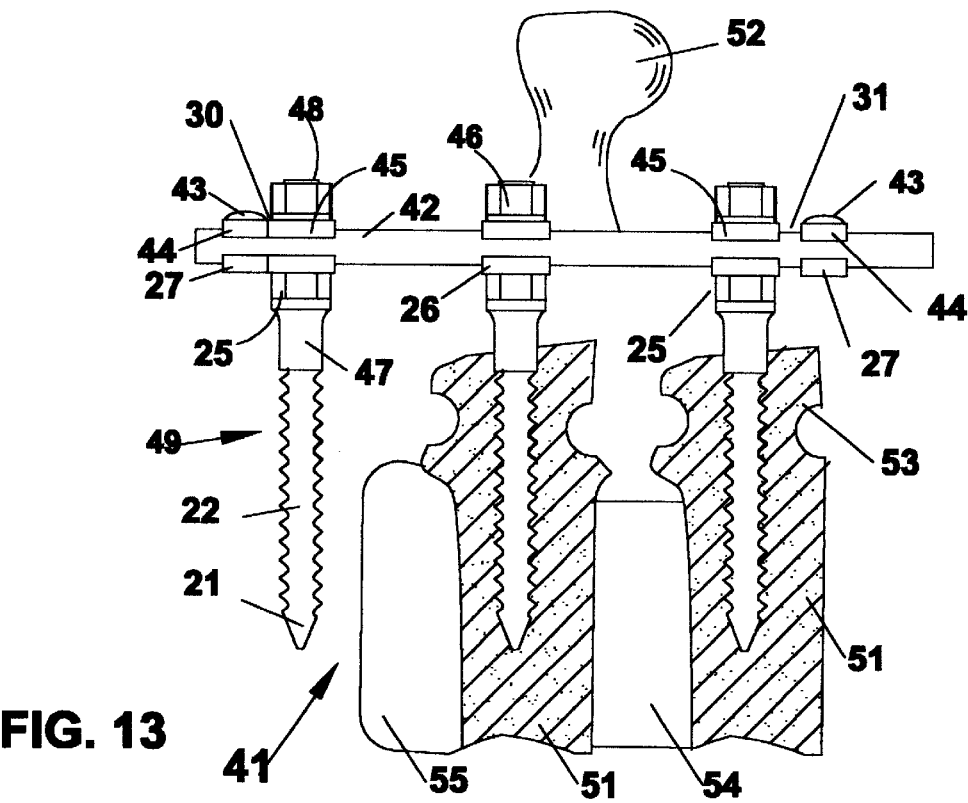
FIG. 13 is a sectional side view taken along the line 13—13 of the system installed in a vertebra.

A bone screw 47 is threaded into a drilled and tapped hole in a selected vertebra 51 shown in FIG. 13. This invention allows the bone screws 47 to be infinitely positioned axially, to place it into the position where it is threaded into a vertebra 51 or graft 54. The anterior side of the plate 42 may be placed temporarily on the bone screw 47 to be used as a template to determine the position and angle of the remaining screw holes. The remaining screws 47 are threaded into the remaining holes. Once the screws are all in place, the lower portion 26 of each bone screw clamp assembly 49 is placed on the clamp end of each bone screw 47. The plate 42 is positioned on the clamp lower portion 26. If desired the bone screws 47 may be tightened, or loosened with a selection of spacer with differing heights. At this point the method of implanting is continued differently, depending upon the desired conditions. A cross-link 64 that connects the right lateral stabilizer to the left lateral stabilizer may be used for greater rigidity.

(a) If a totally rigid system is required, the upper clamp portion 45 and the machine screw nuts 46 are installed and tightened to clamp compression on the plate 42. If additional rigidity is required one or more rigidizing stop locks 28 may be attached or crosslinks may be placed.

Figure 14:
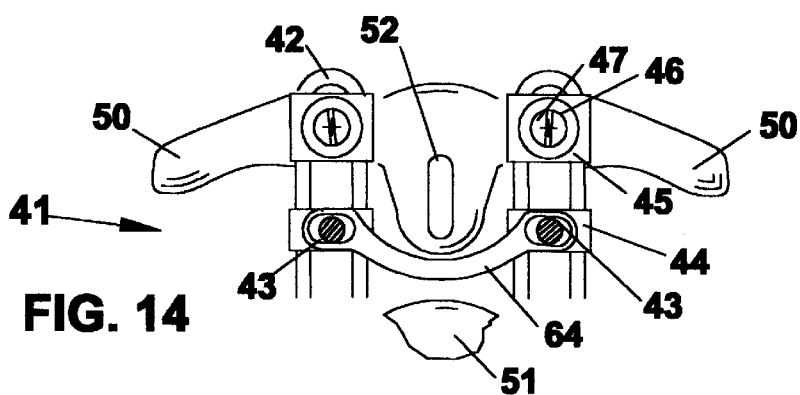
FIG. 14 is a plan view of the system showing an optional cross connector link.
Figure 15:
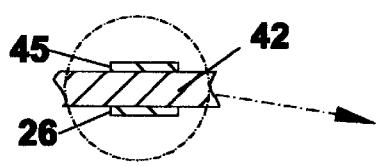
FIG. 15 is a section of the bone screw clamp taken along the line 15—15 FIG. 11.

(b) If a bi-directional dynamized action is desired, spacers 60 are placed over each bone screw 47 requiring dynamized action, as shown in FIG. 7. The upper clamp 45 and nut 46 are set in place and tightened to compress against the spacer 60 and lower clamp portion 26, maintaining clearance between the plate 42 and the bone screw clamp portion. If additional rigidity is required, one or more rigidizing stop locks 28 may be attached with a space 31 between bone screw assembly 49 and the rigidizing stop lock. Cross links may also be placed as shown in FIG. 14.

(c) If unidirectional dynamized (subsidence) action is desired spacers 60, shown in FIG. 7 are placed over each bone screw 47 requiring dynamized action and the upper clamp portion 45 and nut 46 are set in place and tightened to compress against the spacer 60 and lower clamp portions 26. Then rigidizing stop locks 28 are attached and slid along the plate 42 until it abuts at surface 30, shown in FIG. 13, the bone screw clamp assembly 49 and is tightened, preventing motion in the direction of the rigidizing stop lock. If additional rigidity is required one or more rigidizing stop locks 28 may be attached or cross-links 64 may be placed.

(d) If unidirectional preloaded dynamized action is desired, spacers 60, shown in FIG. 7, are placed over each bone screw 47 requiring dynamized action and the upper clamp 45 and nut 46 are set in place and tightened to compression against the spacer 60 and lower clamp portion 26. Next the rigidizing stop locks 28, shown in FIG. 5, are attached and slid along the plate 42 until they abut the bone screw clamp portion 45 and 26. A compression tool means may be used to draw the bone screws 49 toward each other until the desired preload is reached, the rigidizing stop locks 28 are tightened against the bone screw clamps preventing motion in the direction of the rigidizing stop lock 28 and preload is maintained. If additional rigidity is required one or more rigidizing stop locks 28 may be attached or cross links may be placed.

We claim:

1. A dynamized spinal stabilization system for fixing one bone segment with respect to one or more other bone segments within a bone column, said bone column having a longitudinal axis through each said bone segment, said stabilization system comprising:

a. a plate member, having a longitudinal plate axis, for placement upon said bone segments adjacent to and parallel to said bone column longitudinal axis, said plate having two parallel side faces, a through slot parallel to said plate axis;

b. a plurality of bone screws having a threaded portion capable of engaging the said bone segment, having an intermediate portion with a shoulder without threads, and a machine threaded stud portion, said stud portion extend through said slot of said plate member into said bone segment upon installation;

c. a clamp nut which is threaded to engage said machine threaded stud portion of said bone screw;

d. an upper screw clamp which clamps the said bone screw to the said upper face of said plate, said clamp having a clearance hole through which said stud portion will pass freely;

e. a lower screw clamp which clamps said bone screw to the said lower face of said plate, said clamp having a clearance hole through which said stud portion will pass freely;

f. a screw clamp spacer which will clamp said upper clamp and said lower clamp together;

g. a lower stop clamp with flanges to contain said clamp in alignment with said plate side faces, said lower stop clamp having a threaded hole;

h. an upper stop clamp with flanges to contain said clamp in alignment with said plate side faces, said stop clamp having a hole through which a clamp screw will pass;

i. a stop clamp screw which passes through the said upper stop clamp hole and engages the said lower clamp threaded hole;

j. a means for connecting said plate, said bone screw, said bone screw upper and lower clamps, said spacer, said clamp nut, and said upper and lower stop clamp plates, and said stop clamp screw; and k. a graft means to support the body weight above it, which will restore the original space between the said bone segments.

2. The said stabilizer system of claim 1, wherein the said spacer slidably engages said plate slot and extends above said plate, said spacer has one hole, which slidably engages said machine screw threaded stud portion.

3. A dynamized spinal stabilization system of claim 1, further comprising at least a second bone screw, at least a second nut and at least a second upper and lower bone screw clamp.

4. The stabilization system of claim 3, where the bone segments are may be fixed to the plate to maintain position with respect to the plate by omitting said spacer from said bone screw.

5. The stabilization system of claim 3 wherein the bone screw is preloaded to force compression between said bone segments.

6. A method for fixing one or more bone segments in the required relationship, comprising:

a. utilizing said dynamized spinal stabilization system of claim 3;

b. placing said spinal vertebral bones in the said relationship;

c. threading said screws into said bones;

d. placing said lower bone screw clamps onto said bone screws;

e. placing said plate over said bone screws and seating said plate on said lower bone screw clamps;

f. placing said spacer over each dynamized bone screw machine screw threads, and seating said spacer upon each said lower bone screw clamp of the bone screws that are to be dynamized;

g. placing said upper bone screw clamp over each said machine screw thread and seating upper bone screw clamp on said plate; and h. clamping each said upper bone screw clamp with said nut.

7. The method of claim 6, further comprising the step of installing one or more of said stop clamps to preload, the dynamized bone screws, which contain said spacer, against the bone screw clamp thereby compressing the vertebra attached to said bone screw.

8. The method of claim 7 where a space is set between the said stop clamp and the dynamized bone screw clamp for controlling and limiting the movement of said bone screw with respect to said plate along said plate axis.

* * * * *